Aug. 23, 1955 E. B. BRAUNS Plant Pat. 1,411
APPLE TREE
Filed April 5, 1954
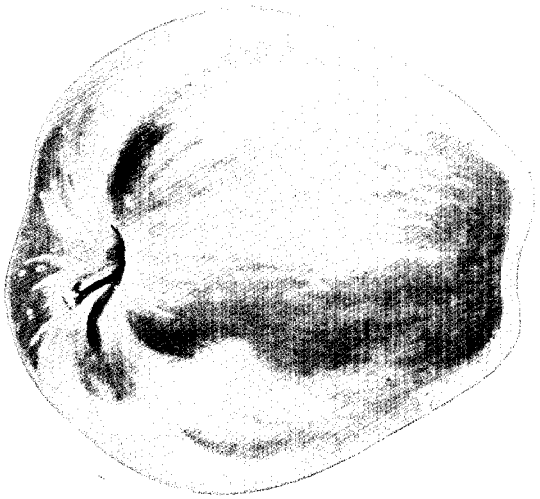
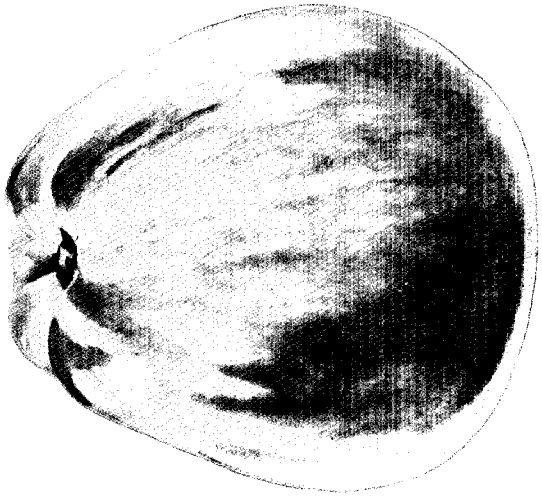
INVENTOR.
E. BARCLAY BRAUNS
BY
Reynolds, Bead & Christensen
ATTORNEYS United States Patent Office Plant Pat. 1,411
Patented Aug. 23, 1955

1,411

APPLE TREE

Edward Barclay Brauns, Wenatchee, Wash., assignor to Van Well Nursery, Wenatchee, Wash., a copartnership Application April 5, 1954, Serial No. 421,214

1 Claim. (Cl. 47—62)

This invention or discovery relates to a new and distinct variety of apple tree, originating as a sport or limb mutation on a Starking Delicious apple tree, unpatented, growing in my orchard near Riverside, Washington. This new variety has its nearest resemblance to the Starking Delicious apple but has readily identified characteristics clearly distinguishing it therefrom as hereinafter described.

The Starking Delicious tree which originated as a sport or mutation from the Standard Delicious, unpatented, is widely grown in many commercial apple sections of the world. Among other characteristics which distinguish Starking from Standard Delicious, its fruits are superior in the amount of red color developed. My new and distinct variety herein described produces fruits having all the desirable characteristics of the Starking Delicious but with a distinctive and vastly superior skin coloring. The commercial potentialities of this improved variety are therefore exceptionally good.

All but one limb (the sport limb) of the tree on which my new variety originated produces typical Starking fruit. All adjacent trees are Starking Delicious. All of the young trees constituting the second and third generation which were propagated from buds of my new variety are growing adjacent to Starking trees. Accordingly excellent opportunity was afforded for comparing the original and successive generations of the new variety with its nearest related variety. Based on the observations and opinions of experts, it appears that the new variety is indistinguishable from its parent, the Starking Delicious, in all respects except the coloring of the fruit.

The fruit coloring characteristics of Starking Delicious are well known in many fruit growing areas. Under the conditions in my orchard, Starking begins to color appreciably several weeks ahead of the Standard Delicious. At harvest time it possesses a greater quantity of color than the Standard Delicious, as well as varying in the quality of color. The well colored apples of the Starking Delicious are medium to dark red in color while well colored specimens of the Standard Delicious have a distinctly lighter shade of red. The red color on both the Standard and Starking Delicious is striped in nature.

The new variety herein disclosed begins to develop appreciable red color just as far in advance (several weeks) of Starking as Starking to the same degree colors in advance of Standard Delicious. Fruits of this new variety consistently have achieved 75% to 100% red color when adjacent and comparable Starking fruits have achieved not more than 35% red color. At the earliest picking maturity this difference in color advantage is generally less but still extremely obvious. For example, in my orchard by the time substantially all of the apples from trees of this new variety will meet the color requirement for the Extra Fancy grade specified by the Washington State Grading Rules only 25% to 35% of the apples from Starking trees growing adjacent thereto will meet the color requirement for this grade. In the year 1953, for example, the earliest picking date authorized in the State of Washington was September 20. At that time all of the fruit of the trees of this new variety in my orchard were colored sufficiently for top grading and these trees were completely stripped of fruit, whereas only about ten percent of the fruit on Starking trees in the same orchard was colored sufficiently to be picked. From ten days to two weeks longer was required for coloring of Starking fruit before the remainder could be picked. The fruit of this new variety may thus be harvested commencing at a materially earlier date than the earliest permissible harvesting date for the Starking Delicious, and yet the picking seasons for the two varieties terminate at about the same time.

The new variety aside from developing a greater amount of red color than Starking also varies therefrom in its quality of red color. The shade of red which it develops is somewhat darker and the striping is more pronounced than on the Starking fruit. Moreover, it possesses broader stripes than Starking. These stripes are dark red in color deepening to almost purplish red and are interspersed with lighter shades of red. This color pattern results in a very pleasing effect and makes the apple highly attractive. The calyx or basin area colors more uniformly than Starking.

The new variety has been reproduced successively through second and third generations by budding in my orchard at Riverside, Washington. The apples from each of the reproductions clearly have the distinguishing color characteristics of the original sport limb as herein described and illustrated. It therefore appears that these new and different characteristics are permanent as judged by fruits borne on both second and third generation trees.

The accompanying illustrations of the fruit of the new variety are as accurate as it is believed reasonably possible to make them.

The following is a detailed description of the new variety and is based on studies of the original sport limb as well as the second and third generation trees propagated from buds taken from the original limb and the second generation trees respectively.

Tree: The tree, or vegetative growth, is similar in all respects to Starking Delicious.

Fruit: The fruit appears similar to Starking in shape, size, form, texture, flavor, flesh color, season of maturity, and keeping quality.

*Skin color.*—Typical specimens are entirely covered with varying shades of medium to dark red. Moderately broad, irregular stripes of dark red deepening to almost purplish red are interspersed with solid areas of lighter shades of red. Both the basin and cavity areas color in a pattern comparable to the other portions of the skin. The red color on these fruits appears to be divided into two parts. The first color is deposited on the green ground color of the fruit in the form of flakes of red color. These flakes, when examined individually, approach pomegranate purple. This color is listed on Plate 12 in Color Standards and Nomenclature by Ridgeway. When this light portion of the apple is observed it is possible to see the ground color, or the yellow color, appearing through these flakes of red so that the general impression is of rose-red. Overspreading this color is the second color of the fruit which is in the form of stripes of varying width of a darker color. The color of these stripes is as dark as Bordeaux, also shown on Plate 12. These colors are so heavy that the lighter colors do not show through. In some specimens these stripes are so close together as to cause the fruit to appear to be completely covered with them. In other specimens the light colored areas show between the stripes of darker colored material. It should be pointed out that these darker stripes are not chimeras, but are merely stripes of red color of varying width and length.

Having thus disclosed my improved variety, I claim: A new and distinct variety of apple tree characterized as to novelty primarily by the earlier and greater coloring of its fruit by which it is clearly distinguishable from the nearest related variety, the Starking Delicious, substantially as shown and described.

No references cited.